USOO5865758A

United States Patent [19]
Louzianine

[11] Patent Number: 5,865,758
[45] Date of Patent: Feb. 2, 1999

[54] SYSTEM FOR OBTAINING HEMODYNAMIC INFORMATION

[75] Inventor: Andrei G. Louzianine, Sochi, Russian Federation

[73] Assignee: Nite Q Ltd, Rochester, N.Y.

[21] Appl. No.: 873,280

[22] Filed: Jun. 11, 1997

[30] Foreign Application Priority Data

Jan. 24, 1997 [RU] Russian Federation ............. 97100742

[51] Int. Cl.$^6$ .............................. A61B 5/02; A61B 5/026; A61B 5/021
[52] U.S. Cl. ........................... 600/504; 600/485; 600/526
[58] Field of Search ................................... 600/485, 504, 600/508, 526

[56] References Cited

U.S. PATENT DOCUMENTS

| 4,066,066 | 1/1978 | Paek . |
| 4,562,843 | 1/1986 | Djordevich . |
| 4,790,326 | 12/1988 | Mather . |
| 4,834,107 | 5/1989 | Warner ..................................... 600/526 |
| 5,183,051 | 2/1993 | Kraidin et al. . |
| 5,299,120 | 3/1994 | Kaestle . |
| 5,682,898 | 11/1997 | Aung et al. . |

FOREIGN PATENT DOCUMENTS

| 0014720 | 9/1980 | European Pat. Off. . |
| 0060116 | 9/1982 | European Pat. Off. . |
| 0393228 | 10/1990 | European Pat. Off. . |
| 2262952 | 8/1974 | France . |
| 1791191 | 1/1974 | Germany . |
| 2361173 | 4/1976 | Germany . |
| 2314536 | 1/1977 | Germany . |
| 2460839 | 3/1979 | Germany . |
| 2147368 | 9/1979 | Germany . |
| 9406348 | 3/1994 | WIPO ..................................... 600/526 |

OTHER PUBLICATIONS

SU Inventor's Certificate No. 736955, Cl. A 61B5/02, 1980.
E.I. Zborovsky, Method for Analysis of Energy Spectra of Sphygmogrmas and Experience in Clinical Application of the Results of This Analysis, Novosibirsk, 1971.

Yu. I Gaevsky, Dynamopulsography as a Method for Analysis of Systolic Function of Heart, Function of Aorta Valve, and Resilient Properties of Blood Vessels, PhD Thesis, Perm, 1972.

A.I. Leshchenko, Determination of Stroke vol. of Heart based on Duration of Sphygmic Phase and Frequency of Systoles. "Vrachebnoe Delo", 1973, No. 12, pp. 28–30.

I.M. Kaevitzer, N.P. Paleev, Graphical Methods of Analysis ... and of the Pulse. "Cardiology", 1975, vol. 15, No. 6, pp. 150–155.

Millington, R.F., Radial Arterial Pulse Measurement, J. Appl. Physiol. 1977, vol. 273, No. 2, pp. 25–26.

V.S. Logvinov, Diagnostic Methods based on Parameters of Oscillatory and Harmonic Processes in the Cardiovascular System. Pulse–Based Diagnostics In Tibetan Medicine, Novosibirsk, Nauka Pub. 1988 pp. 90–108.

Boronoev, V.B. Poplaukhin, V.N. Pulse–Based Diagnostics in Tibetan Medicine, Tibetan Medicine, Ulan–Ude, 1994, pp. 45–50.

Primary Examiner—William E. Kamm
Assistant Examiner—Carl H. Layno
Attorney, Agent, or Firm—M. Lukacher; K. Lukacher

[57] ABSTRACT

A system (method and apparatus) for hemodynamic measurements of the cardiac activity, including the stroke volume and cardiac output on the basis of a blood pressure pulse wave of a patient. Using a function that relates cardiac activity to an anthropometric parameter of the patient (height or arm span), ordinates of the pulse wave, and time intervals of certain characteristic points of the pulse wave, the stroke volume and/or cardiac output are obtained. The pulse wave can be determined by means of an optical sensor clipped to an ear lobe of the patient. The characteristic points and time intervals from the initial point of the pulse wave to the characteristic points are obtained under computer control. The measured values of the time intervals and ordinates are inputted to the computer which computes cardiac output, stroke volume and other cardiac information related thereto.

20 Claims, 3 Drawing Sheets

SYSTEM FOR OBTAINING HEMODYNAMIC INFORMATION

FIELD OF THE INVENTION

The invention relates to a system (method and apparatus) for obtaining hemodynamic information from human subjects and other animals (biological objects), and particularly to a system for measuring, non invasively and continuously, heart stroke volume, cardiac output, heart rate, and values of other cardiac activity.

BACKGROUND OF THE INVENTION

Cardiac output, i.e., the amount of blood ejected from the left ventricle into the systemic circulation per minute, is one of parameters which is very important for controlling the condition of a cardiovascular system of a human being or any mammal. This parameter is important in anesthesiology, intensive care, during surgery, and in similar situations where continuous control of cardiac activity of a patient is critical.

At the present time the existing methods for measuring cardiac output may be divided generally into invasive methods and noninvasive methods. Each of the above categories, in turn, can be classified on the basis of the principles on which the methods are based upon. For example, invasive methods may be subdivided into thermodilution methods, dye dilution methods, etc. Among these, thermodilution methods for measuring cardiac output are the most simple and accurate methods which, therefore, find most frequent application in the field of hemodynamics. In accordance with these methods, a cardiac catheter, e.g. a Swan-Ganz type catheter, is introduced into the lung artery and is used for measuring the cardiac output (see an article by J. Conway and P. Lund-Johansen in "European Heart Journal", 1990, 11, p. 17). Measurements by thermodilution methods have an accuracy within the range of 10–15%. In measuring parameters of hemodynamics, thermodilution is considered by clinicians to be a "Gold Standard", i.e. a generally accepted way of making hemodynamic measurements.

However, a disadvantage of this method, as well as any other invasive methods, is that it requires an introduction of a catheter into the cardiovascular system of a patient. It is known that long dwelling of the catheter in the patient's body may lead to complications. Another disadvantage of all invasive methods is their high cost and requirements for highly trained personnel. Thermodilution, e.g., as it is commonly practiced, provides discrete measurements, rather than continuous monitoring of cardiac output.

Noninvasive methods of making hemodynamics measurements, such as cardiac output, etc., in general, can be divided into ultrasound methods, echocardiography methods and impedance methods, etc.

Typically, an impedance method is carried out with several electrodes which are brought into contact with a part of the patient's body, e.g., with the neck, and/or the abdominal area. Then a high-frequency current (e.g., of about 1 to 5 mA, 50 to 200 kHz) is passed between the electrodes through the body, and the impedance of part of the body is continuously measured. The impedance method is based on the principle that when blood vessels are completely filled with blood during the cardiac impulse, the body has the minimum impedance, and at the moment directly prior to the cardiac impulse, when blood vessels have minimum volume of blood, the impedance of the body is at its maximum. The difference between the maximum and minimum impedances is proportional to a heart stroke volume (hereinafter referred to as "stroke volume"). The stroke volume is the volume of blood ejected by the left ventricle during a single systole. After appropriate calibration, an absolute value of stroke volume is obtained (S. W. White, et al. European Heart Journal, 1990, 11, p. 79).

A drawback of the impedance method is that when carried out simultaneously with the introduction of various substances into the patient's body which possess electrolytic properties (e.g., a physiological solution) the measurement is inaccurate. Similar inaccuracies occur with the loss of blood. Furthermore, the impedance method is inconvenient and expensive because it involves a complicated procedure of installating sensors over the patient's body.

In another noninvasive method, stroke volume may be measured in terms of the duration of a sphygmic phase and heart rate. See Leshchenko A. I. in Russian Journal "Vrachebnoe Delo", 1973, No. 12, pp. 28–30. The sphygmic phase is a period of time from opening to closing of the aorta valve. Heart rate is the number of ventricular contractions per minute. In accordance with this method, the stroke volume is calculated by means of the following equation:

$$SV = a \cdot T + b \cdot HR - c,$$

where a, b, and c are constants which are determined experimentally, T is the duration of the sphygmic phase, and HR is the heart rate. The accuracy of measurement with this method, as well as all other known noninvasive methods, has been found insufficient for widespread, practical application.

OBJECTS AND SUMMARY OF THE INVENTION

It is an object of the present invention to provide improved system (method and apparatus) for acquiring hemodynamic information.

It is still another object of the invention to provide an improved, computerized instrument whereby determination of the stroke volume and cardiac output may be effected.

It is still another object of the invention to provide an improved system for noninvasive, continuous measurement of the cardiac activity of a patient to facilitate control by the physician of such activity especially in critical situations.

Still another object is to provide an improved system for cardiac activity measurement which does not depend on introduction of various substances into the patient's body, loss of blood, and the like.

These foregoing and other objects, features and advantages of the invention and the best mode now known for carrying out the invention will become more apparent from the ensuing description when read in connection with the following drawings.

Briefly described, a system embodying the invention determines stroke volume and cardiac output from a blood-pressure pulse wave which is obtained from the cardiovascular system of a subject. It has been discovered in accordance with the invention, that the stroke volume and/or cardiac output is related to certain anthropometric parameters of biological objects and ordinates and time intervals of certain characteristic points on the blood-pressure pulse wave. The relationship constitutes a function or algorithm from which cardiac output can be obtained, rapidly and noninvasively, especially with a computer and under computer control. The blood-pressure pulse wave from the subject is measured. A plurality of characteristic points on the pulse wave are accessed by detecting when the wave exhibits certain characteristics, namely the beginning of the wave, the maximum of its first derivative, its maximum amplitude, the minimum of its first derivative and the end of the wave. The timing of aforementioned characteristic points, particularly the durations of intervals from the initial point of the pulse wave and the ordinates of the pulse wave at the characteristic points are measured. The stroke volume and/or cardiac output for the biological object are computed from these measurements. The measurements and computation may be repeated for each successive heart stroke.

Apparatus embodying the invention has a pulse wave measuring unit, a data acquisition unit, a computer, and an indicator unit. The data acquisition unit has a pulse-wave minimum/maximum measuring unit, an ordinate measuring unit, a differentiating unit, a time interval measuring unit, and a pulse-wave derivative minimum/maximum measuring unit. These units are preferably implemented in the computer via software, i.e., programming of the computer. The characteristic points are located by the computer which operate to provide the measuring units. The measurements are thereby accessed and the cardiac output for each pulse wave is computed in the computer.

DETAILED DESCRIPTION OF THE INVENTION

Consider first the method and algorithm provided by the invention. The consecutive steps of the method will be described separately in detail with reference to specific relationships (equations).

The method and algorithm of the invention for determining the stroke volume and cardiac output on the basis of a blood-pressure pulse wave of a biological object is carried out by monitoring of the cardiovascular system. Generally the steps of the method are: 1) providing a function that determines a dependence of the stroke volume and/or cardiac output from an anatomical parameter of the biological object, e.g., an anthropometric parameter such as height for humans, and ordinates and time intervals of the characteristic points on the blood-pressure pulse wave; 2) measuring the blood-pressure pulse wave of the biological object; 3) determining five characteristic points on the pulse wave; 4) measuring time intervals from the initial point of the pulse wave to each characteristic point and measuring the ordinates of the pulse wave at the characteristic points; 5) entering the measured values of time intervals and ordinates of the characteristic points into the aforementioned function; 6) calculating the stroke volume and/or cardiac output for the biological object; and 7) repeating the aforementioned steps for each heart stroke. The function describes a mathematical model of the cardiovascular system of the biological object which has been verified experimentally, as discussed hereinafter.

Figure 1:
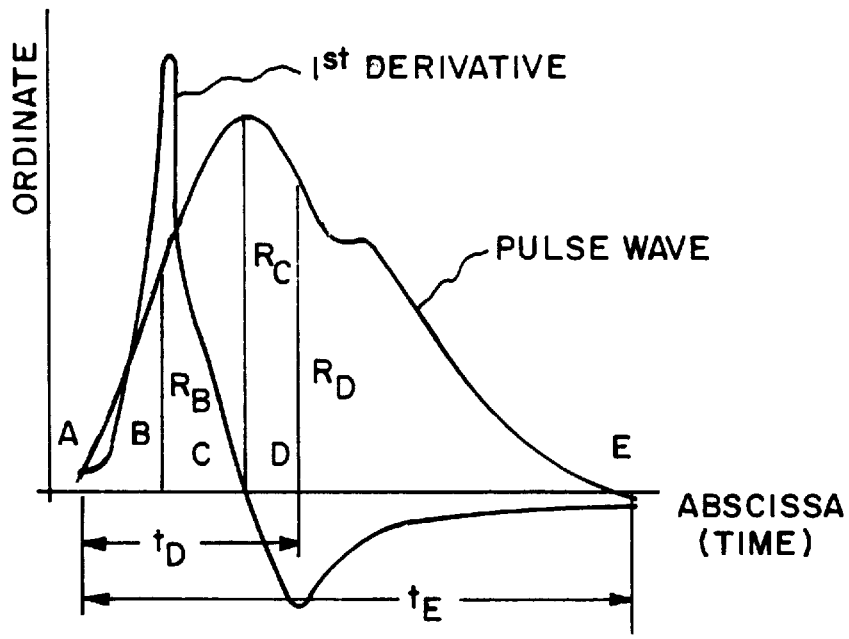
FIG. 1 is a plot with time, as the abscissa axis, and magnitude as the ordinate axis of a typical blood-pressure pulse wave and the first derivative of that wave, illustrating characteristic points, the timing and ordinates (amplitudes), the values of which are used in computing cardiac output in accordance with the invention.

In Step 1, a function is provided, which describes the mathematical model, and relates the cardiac output from anatomical parameters of the biological object (for humans this may be the so-called anthropometric parameters), ordinates of the pulse wave, and timing of the characteristic points. A typical blood-pressure pulse wave is shown in FIG. 1 where time is plotted on the abscissa axis and ordinates of the pulse wave are plotted on the ordinate axis. The following characteristic points of the waveform are shown in FIG. 1: point A—beginning of the wave; point B—maximum of the first derivative of the waveform (at this point, the speed of propagation of the pulse wave along the walls of the arterial blood vessels is maximal), the ordinate of the pulse wave at this point is designated $R_B$; point C is the point where the amplitude of the wave is at its maximum (i.e., of the maximum ordinate), thus ordinate of the pulse wave is designated $R_C$; point D is a point of the minimal value of the first derivative (the moment of closing of the aortal valve), the ordinate of the pulse wave in the point is designated $R_D$; point E—is at the end of the wave and beginning, i.e., point A, of the next pulse. The timing of points B, C, D, and E are measured as the intervals from point A which is the beginning of the pulse wave and are designated $t_B$, $t_C$, $t_D$, $t_E$, respectively. It should be noted that aforementioned ordinates of the pulse wave in points B and D are measured in relative units as a ratio of an absolute value of the ordinates in these points to the absolute value of the amplitude $R_C$.

CO (cardiac output) and SV (stroke volume) have the following relationship:

$$CO = SV \cdot HR,$$

(HR is a heart rate) in pulses per minute, CO may be in liters and SV may be in liters per minute.

It has been discovered, in accordance with the invention, that the function as expressed in the following equation relates the cardiac output CO and/or stroke volume SV with anthropometric parameters of the biological object, ordinates and time intervals at the aforementioned characteristic points on the blood-pressure pulse wave (since CO and SV are related, only CO will be mentioned in the subsequent equations):

$$CO = f_1(L) \cdot f_2(t_E, t_D, R_B, R_C, R_D) - f_3(t_D, R_B, R_C). \qquad [1]$$

where $t_E$, $t_D$, $R_B$, $R_C$, and $R_D$ are the same as defined above. Consider first $f_1(L)$ in equation 1.

L is an anatomical parameter of the biological object (sometimes called an anthropometric parameter herein). It has been discovered that, in mammals, a certain empirical relationship exists between CO and various anatomical parameters. An anatomical parameter for a human being are such characteristics as height H, the arm span, etc. The following empirical relationship between CO (liters/min) and the height-H (cm) of a human subject has been found suitable:

$$CO = \frac{H^{1.27}}{e^{4.67}} \qquad [2]$$

where "e" is the base of natural logarithms. For human subjects H was selected as the anthropometric parameter. It is understood that equation [2] represents $f_1(L)$ of equation [1]. Generally, $f_1(H) = H^\lambda / e^\theta$, where $\lambda$ varies within the range of 1 to 2, and where $\theta$ varies within the range of 4 to 5. The most accurate results of measurements have been found to be obtained under the following specific conditions:

where $$f_1(L) = f_1(H) = \frac{H^{1.27}}{e^{4.67}}$$

Thus for humans, equation [1] can be represented as follows:

$$CO = f_1(H) \cdot f_2(t_E, t_D, R_B, R_C, R_D) \cdot f_3(t_D, R_B, R_C) \quad [3]$$

Function $f_1(H)$ has a dimension which is liters/min.

In equation [1], $f_2(t_E, t_D, R_B, R_C, R_D)$ is a function which represents cardiac output in relative nondimensional units. In equation [1], $f_1(H)$ is a function which is dimensional and thus introduces a dimensional frame of reference for non-dimensional function $f_2(t_E, t_D, R_B, R_C, R_D)$ and scales the $f_2$ function. In other words, a product of $f_1(H)$ and $f_2(t_E, t_D, R_B, R_C, R_D)$ is dimensional and may be expressed in liters/min.

On the basis of experiments, a specific expression for function $f_2(t_E, t_D, R_B, R_C, R_D)$ has been found which as follow:

$$f_2(t_E, t_D, R_B, R_C, R_D) = \frac{\alpha}{(R_B/R_C) \cdot t_E \cdot t_D} + \frac{\beta \cdot t_D}{(R_D/R_C)} + \frac{\gamma \cdot (R_B/R_C) \cdot (R_D/R_C)}{t_D} \quad [4]$$

In equation [4], $\alpha$, $\beta$, and $\gamma$ are constants. The values of these constants were found experimentally and vary in the following ranges:

$\alpha$ (sec$^2$) varies from 0.01 to 0.1, $\beta$ (sec$^{-1}$) varies from 0.5 to 5, $\gamma$ (sec) varies from 0.05 to 0.5.

If constants $\alpha$, $\beta$, and $\gamma$ are selected outside of the ranges given above, the accuracy of the measurement may be affected.

In equations [1] and [3], the function $f_3(t_D, R_B, R_C)$ is a scaling function which introduces a correction that takes into account the condition of the myocardium in a specific patient.

The condition of the myocardium is different in various individuals, depending on the age, health, etc. For example, a person who experienced a heart attack will have a weaker myocardium than a healthy person who has not experienced a heart attack.

On the basis of experiments and analysis of the data obtained by plotting pulse waves, it was discovered that, as the myocardium weakens, the ordinate at point B lowers.

The scaling function $f_3(t_D, R_B, R_C)$ may be expressed as follows:

$$f_3(t_D, R_B, R_C) = \delta t_D/(R_B/R_C) \quad [5]$$

In this equation, $\delta$ is a constant. The value of this constant $\delta$ (liter·min $^{-1}$·sec$^{-1}$) may vary from 1 to 10.

In step 2, the blood-pressure pulse wave of a biological object is measured. The pulse wave may be measured with an optical ear sensor clipped to the patient's ear. The pulse waves shown in FIG. 1 were acquired optically from the ear lobe clip sensor. The measurement may be provided by the optical ear sensor and the signal acquisition unit. Analog signals from the sensor may be digitized in the computer which then effects the signal acquisition process to provide the characteristic points and their timing and ordinate values. The apparatus will be described in greater detail hereinafter.

In step 3, five characteristic points on the pulse wave are found. These points are points A, B, C, D, E described above (point E is the end of the pulse wave and the beginning of the next pulse wave). These points are located by detecting the maximum and minimum values of the pulse wave and its first derivative and the start and end of the wave. The implementation shown in FIG. 2. may use analog circuits but, as mentioned, computerized detection techniques may be used.

In step 4, the computer determines the locations, and using timers, derives the time intervals to the characteristic points from the initial point of the pulse. This step also involves the measurement of the ordinates of the pulse wave at the characteristic points.

In step 5, the measured values of time intervals and ordinates of the characteristic points are used in the computer, to calculate cardiac output.

In step 6, the stroke volume and/or cardiac output of the biological object are calculated with equation [3]. For this purpose, the specific values of the ordinates and time intervals obtained in steps 3, 4, and 5 are accessed and used in the computation pursuant to the algorithm expressed in equation [3]. This step corresponds to the completion of one cardiac cycle.

In step 7, the aforementioned steps 2 through 6 may repeat for each successive heart stroke, thereby providing for continuous monitoring and measurement of cardiac activity.

Figure 2:
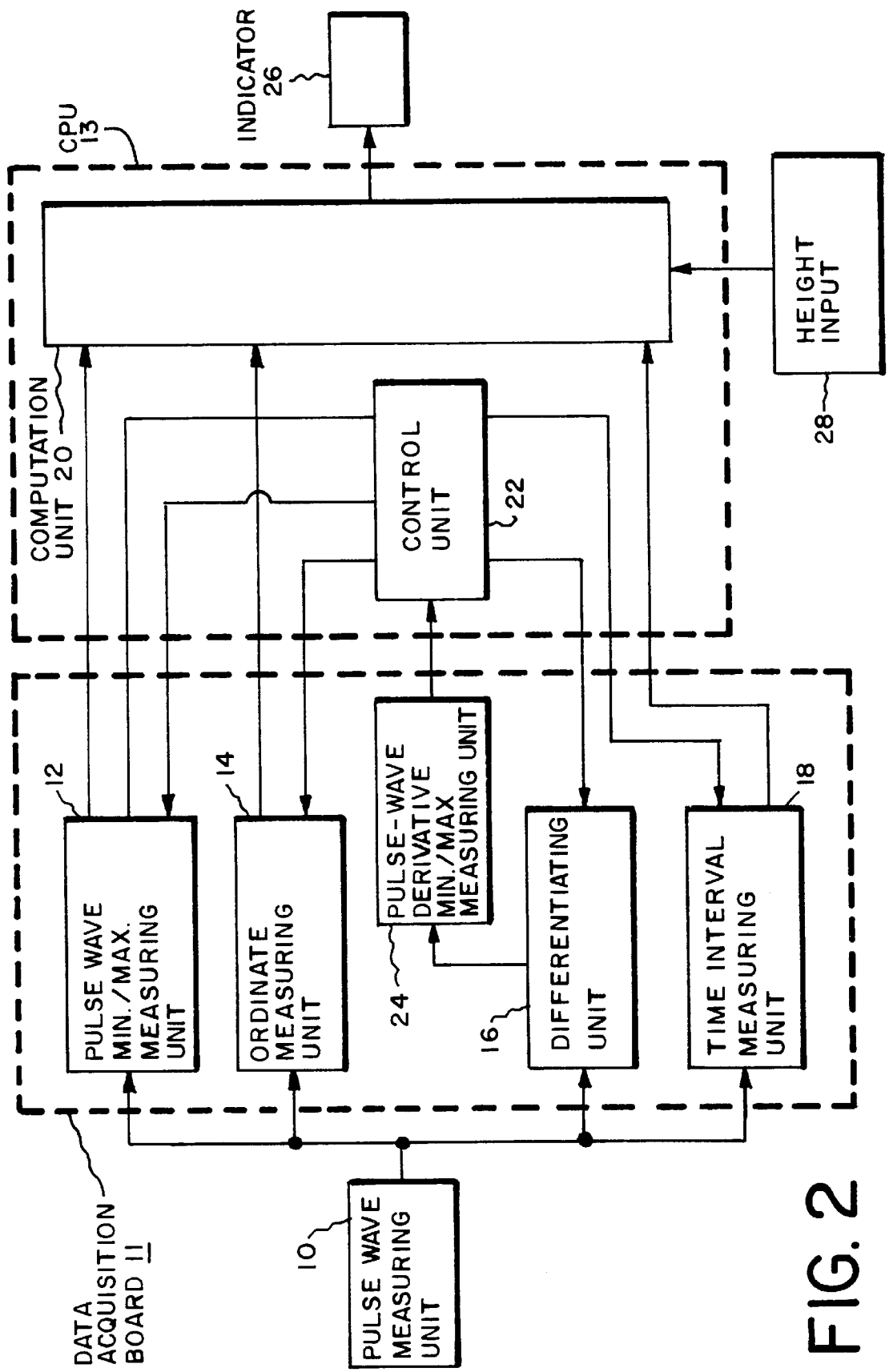
FIG. 2 is functional block-diagram of an apparatus embodying the invention.

Referring to FIG. 2, there are four main components: a pulse wave measuring unit 10, a data acquisition "module" or board II, a central processing unit (CPU) 13 and an indicator/display unit 26. The programming (software) of the CPU is given on the flow chart of FIG. 2A. The computations of cardiac output and stroke volume are also made in the central processing unit 13. The determination of the time intervals and ordinates (i.e., the functions of the data acquisition board 11) may also be implemented in the CPU 13. The indicator (display) unit 26 displays pulse rate, cardiac output and stroke volume (the measurements of cardiac activity).

Data acquisition board has a pulse-wave minimum/maximum measuring unit 12, an ordinate measuring unit 14, a differentiating unit 16, a time interval measuring unit 18, and a pulse-wave derivative minimum/maximum measuring unit 24. The unit 18 provides the timing, i.e., the intervals $t_B$, $t_C$, $t_D$, and $t_E$.

The pulse wave measuring unit or sensor 10 provides the pulse wave (PW) to a pulse-wave minimum/maximum measuring unit 12, ordinate measuring unit 14, and differentiating unit 16. These units and time interval measuring unit 18 are operated by the control unit 22. The differentiating unit provides the first derivative PWD to a pulse-wave derivative minimum/maximum measuring unit 24. Outputs of the units 12, 24 and the PW are used by the control unit 22 to operate units 12 and 18, to provide the R and T inputs to the computation unit 20, which operates to the indicator unit 26 to display, continuously, cardiac output stroke volume and other cardiac activity.

Figure 3:
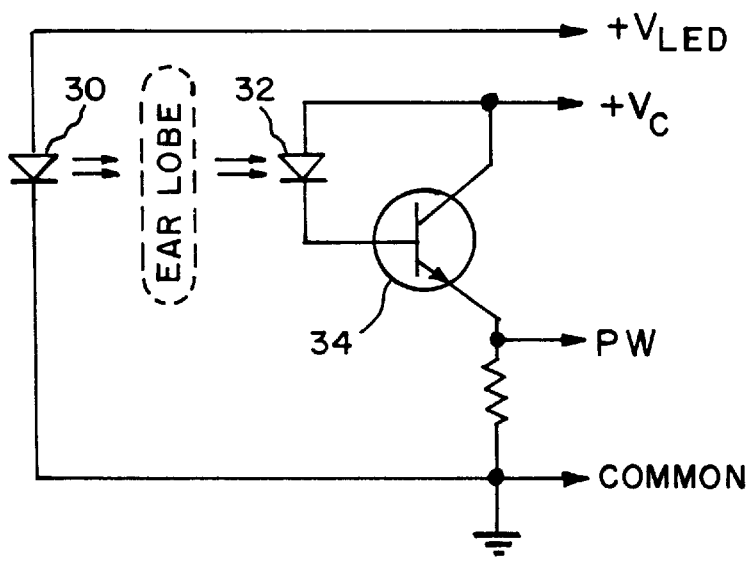
FIG. 3 is a schematic diagram of a sensor used in the apparatus shown in FIG. 2.

Referring to FIG. 3, wave measuring unit 10 is an ear sensor shown as a clip easily fixed on the patients' ear lobe. The sensor 10 has an infrared radiation source such as a light emitting diode (LED) 30 which emits light that passes through the ear lobe of the patient. The light is detected by a photo-detector-such as a photo-diode 32. A photo-current amplifier 34 processes the signal from the photo-detector and provides the pulse wave signal (PW). Control unit 22 processes the obtained information in accordance with program in the computer and controls operations of pulse-wave minimum/maximum measuring unit 12, ordinate measuring unit 14, differentiating unit 16, and time interval measuring unit 18. In response to commands obtained from control unit 22, pulse-wave minimum/maximum measuring unit 12, ordinate measuring unit 14, and time interval measuring unit 18 send signals the computation unit 20 which drives the indicator unit 26 which displays one or more screens of the cardiac activity in real time. Different displays may be provided and SV and other cardiac activity displayed and monitored. These displays give a physician information for control of a patient's cardiac activity. The units of the data acquisition board are preferably implemented in a microprocessor programmed to carry out the functions of these units on the PW. The computation unit 20 has a computer co-microprocessor which may be programmed to provide the function of the data acquisition board and the computation unit 20. Suitable programing for that computer is shown in the flow chart of FIG. 2A.

Figure 2A:
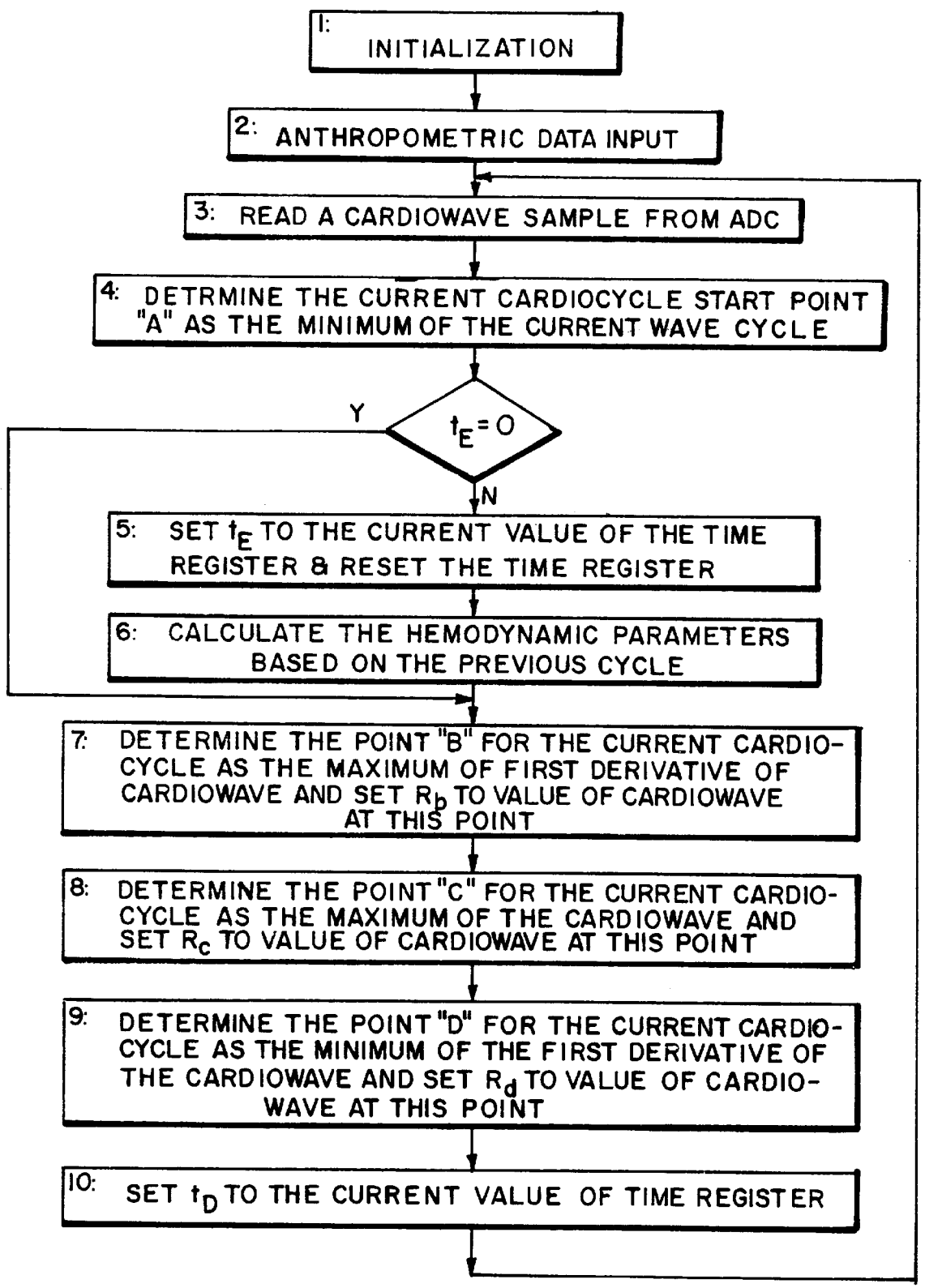
FIG. 2A is a flow chart of the program used in the central processing unit shown in FIG. 2.

Referring to FIG. 2A, the first step of the program is initialization. During this step, all of the registers of the computer are set to zero. The analog to digital converter is initialized to start providing a stream of data, suitably at a 200 Hz rate, when a readable pulse wave is provided from the sensor clipped to the ear lobe.

In the second step, the anthropometric data input is read. As stated above, this is a keyboard input which gives the height of the patient.

As the bytes of data from the ADC are read, they are compared successively until the minimum value of the pulse wave is determined. This is taken as the start point of the pulse wave or cardiocycle. The determination of the cardiocycle start point as the minimum of the current or ongoing pulse wave cycle is carried out in step three of the program.

In step 4, the end of the pulse wave and the beginning of the next pulse wave is considered coincidental and that time value $t_E$ is stored in the time register. The time register is reset.

In the next step, 5, the cardio output and other hemodynamic parameters, particularly stroke volume are computed from the cardiac output. On the first cycle, $t_E$ is zero and, as indicated in the decision block, 4a, the calculation in step 6 bypassed on the first cycle. The calculation includes the stroke volume which is calculated as the cardiac output divided by the heart rate. The heart rate is 60 divided by $t_E$. These values are all stored in the registers of the computer.

In step 6, the successive values of the pulse wave signal are used to calculate the first derivative of the wave. $t_B$ corresponds to time intervals from the start of the cardio wave to the maximum of the first derivative of the cardio wave. The maximum of the first derivative is $R_B$ which is stored in the memory of the computer.

In step 7, the pulse wave bytes from the analog to digital converter are also examined to determine the point C where the pulse wave has its maximum. The value of the ordinate $R_C$ at the maximum is stored in the memory of the computer.

The minimum of the first derivative is computed in step 8 and the value of the ordinate $R_D$ of this first derivative minimum is also stored in memory. The time interval $t_D$ corresponding to point D is also read and stored in the register. All of the values from steps 6, 7, 8 and 9 are utilized in the computation of the cardio output and stroke volume on the next audio cycle. This is indicated on the flow chart by the return of the values from steps 10 to step 3, where the start of the cycle for the next wave is determined. It will be appreciated that $t_E$ is measured for the current cycle in order that the heart rate may be computed and used to determine the stroke volume on that cycle.

Practical Examples

In an example, total of 84 patients were tested with the system of the invention (Sfumato method—called for the name of the Russian concern which participated in the tests). The tests were conducted at Moscow City Hospital No. 33. For comparison, parallel measurements of cardiac output were carried out by the thermodilution method on 24 patients in the intensive care unit of the aforementioned hospital. Thirteen (13) patients had peritonitis caused by injury and gastrointestinal perforation; 4 patient had combined trauma and shock; 2—multiple rib fracture; 2—severe brain trauma; 1—myocardial infarction; and 2—alcoholic intoxication. Twenty two (22) patients were under the controlled mechanical ventilation of lungs, 2—had the spontaneous breathing. In the dilution method, cardiac output was measured by a Datex AS/3 monitor (produced by Datex Co., Finland). The saline solution or 5%-solution of glucose cooled down to a temperature within the range of −1° C. to +12° C. were used in the thermodilution tests.

Results of the Sfumato and thermodilution tests are compared in Table 1. Another 18 patients were tested in the Scientific Center of Surgery (SCS) of the Russian Academy of Medical Sciences, Moscow. All the patients were tested in the operating room at the beginning of the aortocoronary bypass operation before sternotomia. All the patients were 44–59 years old males with distinct bradycardia (44–55 beats per minute). Parallel measurements of cardiac output by the thermodilution method by Sfumato method were performed, thermodilution used a Baxter 93A-431H-7, 5F catheter (Finland) with an MX-04 monitor (Russia). The 5%-solution of glucose cooled down to +3° C. was used in thermodilution testing.

TABLE 1

| Parameters | Correlation | Standard Deviation (absolute value) | Standard Deviation (%) |
|---|---|---|---|
| Cardiac Output, Hosp. 33 | 0.96 | ±0.43 l/min | ±5.9% |
| Cardiac Output, SCS | 0.93 | ±0.53 l/min | ±10.0% |

In total, 96 comparative measurements were made in this round of tests. Thermodilution method was used as a reference. On average, over the entire range of tests, the deviation between both methods did not exceed 10%.

The second round of tests involved 140 additional patients. The tests were conducted in various clinics (including pediatric clinics) and gave essentially the same results as described above.

Thus it has been shown that the invention provides a system (method and apparatus), for simple, reliable, inexpensive, and accurate noninvasive determination of the stroke volume and cardiac output. The method and apparatus of the invention are suitable for continuous control of the cardiac activity of a patient in critical situations. They produce results which do not depend on the introduction of various substances into the patient's body.

Although the method and invention have been described with reference to specific examples, it is understood that these examples should not be construed as limiting the scope of the invention and are given only for illustrative purposes. Therefore, any modification and changes are possible, provided they do not go beyond the scope of the appended claims. For example, the sensor not necessarily is the ear-lobe type sensor. A sensor that operates on the principle of detecting a reflection, e.g. from the carotid artery, may alternately be used. The anthropometric parameter may be an arm span rather than height. Then the $f_2$ and $f_3$ functions are scaled to reflect the arm span parameter. Other anthropomorphic parameters may be used with appropriate scaling of the other functions. Whereas the examples and the results of tests were related to humans, it is understood that the method and apparatus are applicable to other mammals.

I claim:

1. A method for determining the cardiac activity of a subject, comprising the steps of:
   (a) sensing a blood-pressure pulse wave produced by the subject, which varies in magnitude with time;
   (b) selecting a plurality of characteristic points on said wave;
   (c) measuring time intervals from said initial point of said pulse wave to said characteristic points and measuring corresponding ordinates of said pulse wave at said characteristic points;
   (d) obtaining a value corresponding to said cardiac activity from a function that relates the cardiac activity to at least one anatomical parameter of said subject, the ordinates of said blood-pressure pulse wave, and the time intervals of said biological object.

2. The method of claim 1 wherein method is repeatedly carried out and said value is obtained for each of a plurality of said pulse waves produced by said subject.

3. The method of claim 1 wherein said step of selecting a plurality of characteristic points comprises selecting point A which is the initial point at the beginning of the wave; point B which is the point at the maximum of the first derivative of said pulse wave; point C which is the point where the amplitude of the wave is the maximum; and point D which is where the first derivative of the wave is at its minimum.

4. The method of claim 3, wherein said step of obtaining a value utilizes a function which is represented by the following equation:

$$CO = f_1(L) \cdot f_2(t_E, t_D, R_B, R_C, R_D) - f_3(t_D, R_B, R_C),$$

where CO is said cardiac output, L is said anatomical parameter, $f_1(L)$ is a function of said anatomical parameter, $t_E$ and $t_D$ are time intervals to said points E and D, respectively, from said point A; $R_B$, $R_C$, $R_D$ are values of ordinates of said blood-pressure pulse wave at said points B, C, and D, respectively.

5. The method of claim 4, wherein for a human subject said anatomical parameter L is the height H of said human subject, and where $f_1$ (H) has the following meaning: $f_1(H) = H^\lambda / e^\theta$, where $\lambda$ varies within the range of 1 to 2, and where $\theta$ varies within the range of 4 to 5.

6. The method of claim 5, wherein $\lambda$ is approximately 1.27 and $\theta$ is approximately 4.67.

7. The method of claim 6 where $f_3(t_D, R_B, R_C) = \delta t_D / (R_B/R_C)$, where $\delta$ is a constant, which varies from about 1 to 10.

8. The method of claim 5, where $$f_2(t_E, t_D, R_B, R_C, R_D) = \frac{\alpha}{(R_B/R_C) \cdot t_E \cdot t_D} + \frac{\beta \cdot t_D}{(R_D/R_C)} + \frac{\gamma \cdot (R_B/R_C) \cdot (R_D/R_C)}{t_D}$$

where $\alpha$, $\beta$, and $\gamma$ are constants
and $\alpha$ (sec$^2$) is from about 0.01 to 0.1,
$\beta$ (sec$^{-1}$) is from about 0.5 to 5, and
$\gamma$ (sec) is from about 0.05 to 0.5.

9. The method of claim 8 where $f_3(t_D, R_B, R_C) = \delta t_D / (R_B/R_C)$, where $\delta$ is a constant in the range from about 1–10.

10. The method of claim 1 wherein $f_3$ is a scaling function representing the condition of the myocardium.

11. The method of claim 1 wherein said pulse wave is measured by sensing the transmission of light through an earlobe.

12. The method of claim 1 wherein said pulse wave is measured by optoelectrically sensing light transmitted through the ear lobe of the patient.

13. A method for determining the stroke volume, cardiac output or both stroke volume and cardiac output of a patient on the basis of a blood-pressure pulse waves of said patient, produced on each heart stroke comprising the steps of:
   (a) providing a function presenting a mathematical model of the patient's cardiovascular system that relates cardiac output and at least one anthropometric parameter of said patient, ordinates of said blood-pressure pulse wave, and time intervals of said blood-pressure pulse wave of said patient at a plurality of characteristic points, said characteristic points being the following: point A of the beginning of the wave; point B of the maximum of the first derivative of said pulse wave; point C which is the point the amplitude of which is the maximum ordinate of said pulse wave; point D the point where said first derivative is of the minimal value, and point E which is the end of said pulse wave and the beginning of the next pulse wave, said function being represented by the following equation:

$$CO = f_1(H) \cdot f_2(t_E, t_D, R_B, R_C, R_D) - f_3(t_D, R_B, R_C),$$

where CO is said cardiac output, H is said anthropometric parameter which is the height of said patient, $f_1$ (H) is a function of said height, $t_E$ and $t_D$ are said time intervals from said point A to said points E & D, respectively; $R_B$, $R_C$, $R_D$ are values of ordinates of said blood-pressure pulse wave in said points B, C, and D, respectively; $f_3(t_D, R_B, R_C)$ is a function of $t_D$, $R_B$, $R_C$;
   b) measuring the blood-pressure pulse wave of said patient;
   c) measuring, for said characteristic points, corresponding time intervals from the initial point of said pulse wave and measuring corresponding ordinates of said pulse wave, thus obtaining measured values of said time intervals and measured values of said ordinates;
   d) entering said measured values of said time intervals and said measured values of said ordinates of said characteristic points into said function;
   e) calculating the stroke volume and/or cardiac output for said patient with the use of said function; and
   f) repeating steps (b) to (e) for each said heart stroke.

14. The method of claim 13, wherein $f_1$ (H) has the following meaning: $f_1(H) = H^\lambda / e^\theta$, where $\lambda$ varies within the range of 1 to 2, and $\theta$ varies within the range of 4 to 5.

15. The method of claim 14, where $f_2(t_E, t_D, R_B, R_C, R_D)$ has the following meaning:

$$f_2(t_E, t_D, R_B, R_C, R_D) = \frac{\alpha}{(R_B/R_C) \cdot t_E \cdot t_D} + \frac{\beta \cdot t_D}{(R_D/R_C)} + \frac{\gamma \cdot (R_B/R_C) \cdot (R_D/R_C)}{t_D}$$

where $\alpha$, $\beta$, and $\gamma$ are constants which are in the following ranges:
$\alpha$ (sec$^2$) from 0.01 to 0.1
$\beta$ (sec$^{-1}$) from 0.5 to 5, and
$\gamma$ (sec) from 0.05 to 0.5.

16. The method of claim 15 above where, $f_3(t_D, R_B, R_C) = \delta t_D / (R_B/R_C)$, where $\delta$ is a constant from about 1–10.

17. An apparatus for measuring cardiac activity, stroke volume, or cardiac output of a biological object on the basis of a blood-pressure pulse wave of said biological object, comprising:

a pulse wave measuring unit, a data acquisition unit, a computation unit, and an indicator unit, said pulse wave measuring unit, supplying said wave to said data acquisition unit and said data acquisition unit comprising:

(a) a pulse-wave minimum/maximum measuring unit;
(b) an ordinate measuring unit;
(c) a differentiating unit;
(d) a controller;
(e) a time interval measuring unit; and
(f) a pulse-wave derivative minimum/maximum measuring unit, said controller being responsive to units (a) and (f) and controlling when said units (b), (d) and (e) provide inputs to said computation unit.

18. The apparatus of claim 17, wherein said pulse wave measuring unit comprises an optical ear lobe sensor.

19. The apparatus of claim 17 wherein said data acquisition unit comprises a computer programmed in accordance with a flow chart of (FIG. 2A) to provide the functions of units (a) through (e).

20. The apparatus of claim 19 wherein said computation unit is provided by a computer programmed in accordance with said flow chart to compute said cardiac activity.

* * * * *